(12) United States Patent
Murakami

(10) Patent No.: US 12,023,000 B2
(45) Date of Patent: Jul. 2, 2024

(54) ENDOSCOPE

(71) Applicant: OLYMPUS CORPORATION, Hachioji (JP)

(72) Inventor: Ryosuke Murakami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 503 days.

(21) Appl. No.: 17/365,976

(22) Filed: Jul. 1, 2021

(65) Prior Publication Data

US 2021/0321860 A1 Oct. 21, 2021

Related U.S. Application Data

(63) Continuation of application No. PCT/JP2019/012107, filed on Mar. 22, 2019.

(51) Int. Cl.
*A61B 1/00* (2006.01)
*A61B 1/018* (2006.01)
*A61B 1/05* (2006.01)
*A61B 1/06* (2006.01)

(52) U.S. Cl.
CPC ...... *A61B 1/00096* (2013.01); *A61B 1/00174* (2013.01); *A61B 1/018* (2013.01); *A61B 1/05* (2013.01); *A61B 1/0676* (2013.01)

(58) Field of Classification Search
CPC . A61B 1/00096; A61B 1/00174; A61B 1/018; A61B 1/0676; A61B 1/05; A61B 1/0684; A61B 1/07; A61B 1/00163
See application file for complete search history.

(56) References Cited

FOREIGN PATENT DOCUMENTS

| DE | 102016008851 A1 | * | 8/2017 |
|----|----|----|----|
| JP | H08146307 A | | 6/1996 |
| JP | H105171 A | | 1/1998 |
| JP | 2004016455 A | * | 1/2004 |
| JP | 2004016455 A | | 1/2004 |
| JP | 2004020972 A | | 1/2004 |
| JP | 2007296111 A | | 11/2007 |

(Continued)

OTHER PUBLICATIONS

International Preliminary Report on Patentability (IPRP) (and English language translation thereof) dated Oct. 7, 2021 issued in counterpart International Application No. PCT/JP2019/012107.

(Continued)

*Primary Examiner* — Anh Tuan T Nguyen
*Assistant Examiner* — Timothy Tuan Luu
(74) *Attorney, Agent, or Firm* — Holtz, Holtz & Volek PC

(57) ABSTRACT

An endoscope includes a distal end frame disposed at a distal end of an insertion part; an image pickup unit disposed inside the insertion part; an illumination unit disposed inside the insertion part; and an illumination lens disposed on a side opposite to the illumination unit with the distal end frame interposed therebetween. The illumination lens is a plano-convex lens and disposed with a flat surface thereof facing the illumination unit. The illumination unit has an exit surface in which illumination light emerges, and the following Conditional Expression (1) is satisfied:

$$\arc \sin(n_L \times \sin \theta_L / n_W) \leq \arc \cos((\phi/2)/R) \qquad (1).$$

7 Claims, 9 Drawing Sheets

(56) References Cited

FOREIGN PATENT DOCUMENTS

| WO | WO-2019171642 A1 | * | 9/2019 | ......... | A61B 1/00006 |
| WO | WO-2019175044 A1 | * | 9/2019 | ......... | A61B 1/00096 |

OTHER PUBLICATIONS

International Search Report (ISR) (and English translation thereof) dated May 28, 2019 issued in International Application No. PCT/JP2019/012107.
Written Opinion dated May 28, 2019 issued in International Application No. PCT/JP2019/012107.

* cited by examiner (a)

(b)

ENDOSCOPE

CROSS-REFERENCE TO RELATED APPLICATION

The present application is a continuation application of International Application No. PCT/JP2019/012107 filed on Mar. 22, 2019, the entire contents of which are incorporated herein by reference.

BACKGROUND

Technical Field

The present disclosure relates to an endoscope, in particular, an insertion part of an endoscope.

Description of the Related Art

An endoscope includes an elongated insertion part. A structure of a distal end of the insertion part is disclosed in Japanese Patent Application Laid-open No. 2007-296111 and No. 2004-16455.

In Japanese Patent Application Laid-open No. 2007-296111, an objective optical system and an illumination unit are disposed at a distal end of an insertion part. A rod lens or a plano-convex lens is disposed in the illumination unit.

In Japanese Patent Application Laid-open No. 2004-16455, an objective optical system, a concave lens provided in an illumination window, and a transparent cover are disposed at a distal end of the insertion part. A convex surface is formed in a surface of the transparent cover. The convex surface is positioned in a part covering the illumination window.

SUMMARY

An endoscope according to at least some embodiments of the present disclosure comprises:
a distal end frame disposed at a distal end of an insertion part;
an image pickup unit disposed inside the insertion part;
an illumination unit disposed inside the insertion part; and
an illumination lens disposed on a side opposite to the illumination unit with the distal end frame interposed therebetween, wherein
the illumination lens is a plano-convex lens and disposed with a flat surface thereof facing the illumination unit,
the illumination unit includes an exit surface in which illumination light emerges, and
the following Conditional Expression (1) is satisfied:

$$\arc \sin(n_L \times \sin \theta_L/n_W) \leq \arc \cos((\phi/2)/R) \quad (1)$$

where,
$n_L$ is a refractive index of the illumination lens,
$n_W$ is a refractive index of a medium in a space contacting the illumination lens,
R is a curvature radius of a convex surface of the illumination lens,
$T_S$ is a thickness of the distal end frame,
$\phi$ is a diameter of the illumination lens,
$\theta_L = \arc \cos((\phi/2)/R) - \arc \tan(T_S/L_I)$,
$L_I = \phi/2 + L_X$ when $T_L > 0$ is satisfied, $L_I = \phi + L_{LLmax}$ when $T_L = 0$ is satisfied,
$T_L$ is a distance between the exit surface and the distal end frame,
$L_{LLmax}$ is a maximum distance between an edge of the exit surface positioned in a direction opposite to the image pickup unit and an edge of the illumination lens,
sign of the maximum distance is positive when the exit surface protrudes from the illumination lens, and negative when the exit surface is completely covered with the illumination lens,
$L_X$ is calculated from the following expressions (A), (B), and (C), $$\sin \theta_{X'}/\sin \theta_X = n_L/n_A \quad (A)$$

$$\tan(90°-\theta_X) = T_L/((\phi/2) - L_X + L_{LLmax}) \quad (B)$$

$$\tan(90°-\theta_{X'}) = T_S/((\phi/2) + L_X) \quad (C)$$

where,
$n_A$ is a refractive index of a medium between the exit surface and the distal end frame,
$\theta_X$ is an incident angle of a light beam incident on the distal end frame, and
$\theta_{X'}$ is an angle of emergence of a light beam which emerges from the distal end frame.

DETAILED DESCRIPTION

Prior to the explanation of examples, action and effect of embodiments according to certain aspects of the present disclosure will be described below. In the explanation of the action and effect of the embodiments concretely, the explanation will be made by citing concrete examples. However, similar to a case of the examples to be described later, aspects exemplified thereof are only some of the aspects included in the present disclosure, and there exists a large number of variations in these aspects. Consequently, the present disclosure is not restricted to the aspects that will be exemplified.

An endoscope according to the present embodiment includes a distal end frame disposed at a distal end of an insertion part; an image pickup unit disposed inside the insertion part; an illumination unit disposed inside the insertion part; and an illumination lens disposed on a side opposite to the illumination unit with the distal end frame interposed therebetween. The illumination lens is a plano-convex lens and disposed with a flat surface thereof facing the illumination unit. The illumination unit includes an exit surface in which illumination light emerges, and the following Conditional Expression (1) is satisfied:

$$\arc\sin(n_L \times \sin\theta_L/n_W) \le \arc\cos((\phi/2)/R) \qquad (1)$$

where, $n_L$ is a refractive index of the illumination lens, $n_W$ is a refractive index of a medium in a space contacting the illumination lens, R is a curvature radius of a convex surface of the illumination lens, $T_S$ is a thickness of the distal end frame, $\phi$ is a diameter of the illumination lens, $\theta_L = \arc\cos((\phi/2)/R) - \arc\tan(T_S/L_I)$, $L_I = \phi/2 + L_X$ when $T_L > 0$ is satisfied, $L_I = \phi + L_{LLmax}$ when $T_L = 0$ is satisfied, $T_L$ is a distance between the exit surface and the distal end frame, $L_{LLmax}$ is a maximum distance between an edge of the exit surface positioned in a direction opposite to the image pickup unit and an edge of the illumination lens, sign of the maximum distance is positive when the exit surface protrudes from the illumination lens, and negative when the exit surface is completely covered with the illumination lens, $L_X$ is calculated from the following expressions (A), (B), and (C), $$\sin\theta_X'/\sin\theta_X = n_L/n_A \qquad (A)$$

$$\tan(90°-\theta_X) = T_L/((\phi/2) - L_X + L_{LLmax}) \qquad (B)$$

$$\tan(90°-\theta_X') = T_S/((\phi/2) + L_X) \qquad (C)$$

where, $n_A$ is a refractive index of a medium between the exit surface and the distal end frame, $\theta_X$ is an incident angle of a light beam incident on the distal end frame, and $\theta_X'$ is an angle of emergence of a light beam which emerges from the distal end frame.

Figure 1A:
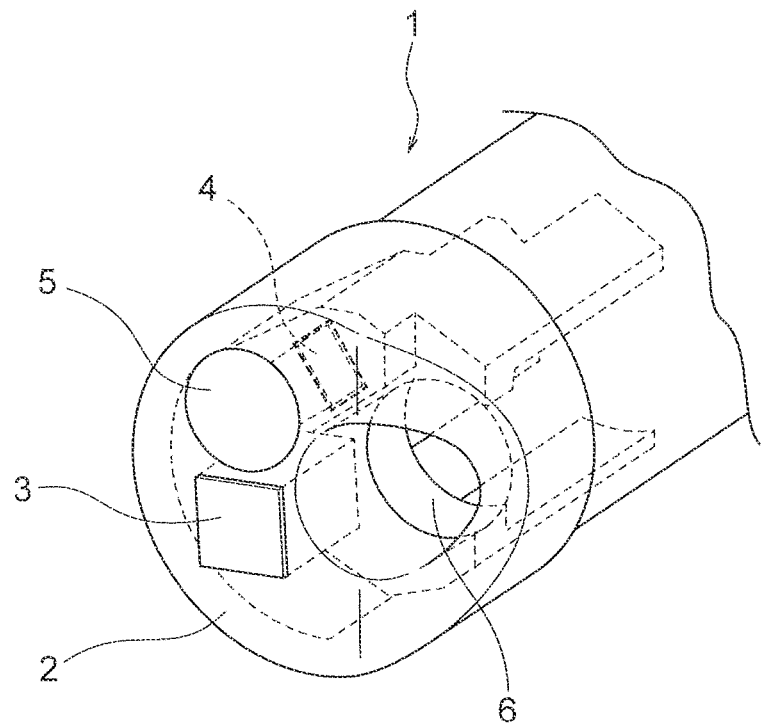
FIG. 1A and FIG. 1B are diagrams illustrating an insertion part of an endoscope according to the present embodiment.
Figure 1B:
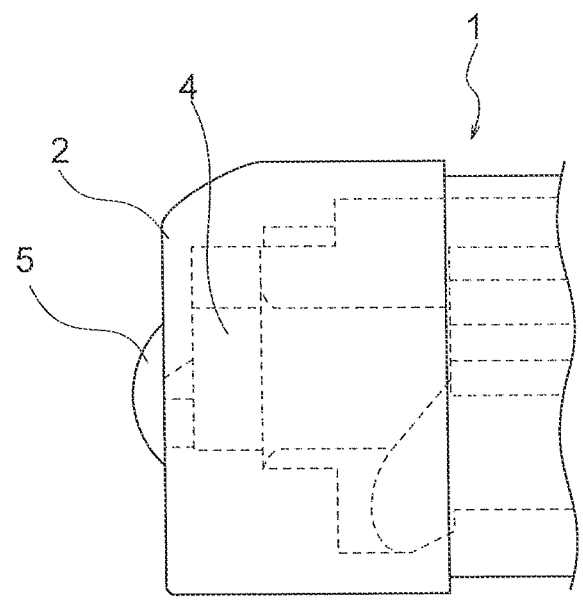

FIG. 1A and FIG. 1B are diagrams illustrating an insertion part of an endoscope according to the present embodiment. FIG. 1A is a perspective view of the insertion part, and FIG. 1B is a sectional view of the insertion part.

The endoscope according to the present embodiment is used for, for example, observation of inside of the body cavity or observation of inside of a metal tube. At a time of observation, an insertion part 1 of the endoscope is inserted into the body cavity or a tube. A distal end of the insertion part 1 is opposed to an object. The object is, for example, a biological tissue or an inner surface of the tube.

A distal end frame 2, an image pickup unit 3, an illumination unit 4, and an illumination lens 5 are disposed in the insertion part 1. A forceps channel 6 can be provided in the insertion part 1. However, the forceps channel 6 is not necessarily provided.

The distal end frame 2 is disposed at a distal end of the insertion part 1. The image pickup unit 3 and the illumination unit 4 are disposed inside the insertion part 1. The illumination lens 5 is disposed on a side opposite to the illumination unit 4 with the distal end frame 2 interposed therebetween. Accordingly, the distal end frame 2 is positioned between the illumination lens 5 and the illumination unit 4.

The illumination lens 5 is a plano-convex lens and disposed with a flat surface thereof facing the illumination unit 4. Accordingly, a convex surface of the illumination lens 5 is opposed to an object. The flat surface of the illumination lens 5 is opposed to the distal end frame 2.

The illumination unit 4 has an exit surface in which illumination light emerges. The exit surface is a light exit surface of a light emission element, or an exit surface of a light guide member. As the light emission element, for example, it is possible to use a LED or a semiconductor laser. As the light guide member, for example, it is possible to use an optical fiber or an optical fiber bundle.

The distal end frame 2 is formed of a plate-like member and a cylindrical member. The plate-like member is positioned at one end of the cylindrical member. The image pickup unit 3 and the illumination unit 4 are disposed in a space surrounded by the plate-like member and the cylindrical member. When the forceps channel 6 is provided in the insertion part 1, a through hole is formed in the plate-like member.

Illumination light emerges from the illumination unit 4. The illumination light is incident on the plate-like member. The plate-like member includes a region which transmits light (hereinafter referred to as "transmission region"). The illumination unit 4 is disposed in a position opposed to the transmission region. Accordingly, the illumination light is transmitted through the plate-like member.

As described above, the illumination lens 5 is disposed on a side opposite to the illumination unit 4 with the distal end frame 2 interposed therebetween. In addition, the illumination lens 5 is disposed in a position opposed to the transmission region. For this reason, the illumination light transmitted through the flat surface of the illumination lens 5 is incident on the illumination lens 5. The illumination light incident on the illumination lens 5 emerges from the illumination lens 5.

As described above, the distal end of the insertion part 1 is opposed to the object. Because the distal end frame 2 is disposed at the distal end of the insertion part 1, the distal end frame 2 is opposed to the object. In this case, because the illumination lens 5 is also opposed to the object, illumination light is irradiated to the object.

The light reflected with the object is incident on the plate-like member. The image pickup unit 3 is disposed in a position opposed to the transmission region. For this reason, the light incident on the plate-like member is incident on the image pickup unit 3.

The image pickup unit 3 includes an image formation optical system (not illustrated) and an image pickup element. With the image formation optical system, an optical image of the object is formed on an image pickup surface of the image pickup element. The optical image is captured with the image pickup element. In this manner, it is possible to acquire an image of the object. For example, it is possible to use a CCD or a CMOS as the image pickup element.

The diameter of the insertion part 1 depends on the area of the plate-like member. It is possible to reduce the diameter of the insertion part 1 by reducing the area of the plate-like member.

The image pickup unit 3 and the illumination unit 4 are disposed side by side. For this reason, when the area of the plate-like member is reduced, an interval between the image pickup unit 3 and the illumination unit 4 is narrowed. The illumination lens 5 is opposed to the illumination unit 4, with the plate-like member interposed therebetween. For this reason, when the area of the plate-like member is reduced, an interval between the image pickup unit 3 and the illumination lens 5 is also narrowed.

As described above, it is possible to use a LED as the illumination unit 4. Because a LED is a light emission element having a wide radiation angle, a light exit surface of an LED is suitable for the illumination unit 4. The flat surface of the illumination lens 5 is opposed to the illumination unit 4. Therefore, it is possible to collect the illumination light which emerged from the illumination unit 4 with the illumination lens 5 efficiently.

However, when the radiation angle is wide, the illumination light which emerged from the illumination lens 5 is easily made incident on the image pickup unit 3 directly. In addition, when the distance between the image pickup unit 3 and the illumination unit 4 is shortened, the illumination light which emerged from the illumination lens 5 is easily made incident on the image pickup unit 3 directly.

The illumination light directly incident on the image pickup unit 3 can generate a ghost or generate of a flare. The generation of a ghost or a flare degrades the image quality.

Figure 2A:
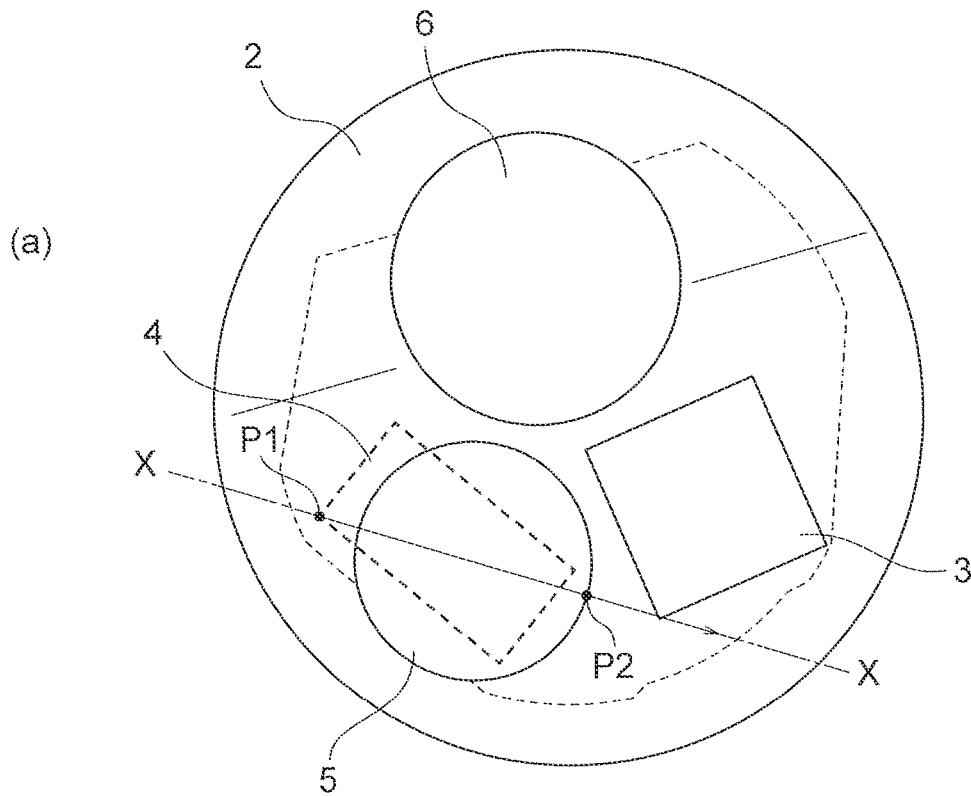
FIG. 2A and FIG. 2B are diagrams illustrating a distal end portion of the endoscope according to the present embodiment.
Figure 2B:
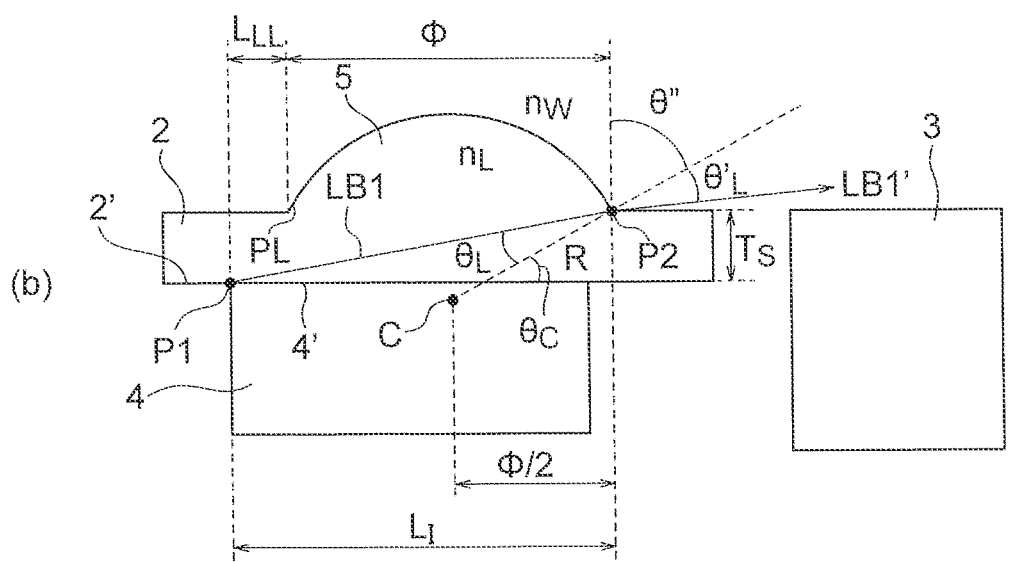

The illumination light which emerges from the illumination lens 5 will be explained hereinafter. FIG. 2A and FIG. 2B are diagrams illustrating a distal end portion of the endoscope according to the present embodiment. FIG. 2A is a front view of the distal end portion of a first example, and FIG. 2B is a sectional view of the distal end portion of the first example.

In FIG. 2A and FIG. 2B, illumination light LB1 and illumination light LB1' are illustrated with solid lines. The sectional view illustrated in FIG. 2B is a sectional view taken along a straight line X-X illustrated in FIG. 2A. The straight line X-X indicates a position of a section. FIG. 2B illustrates parameters used in the Conditional Expression (1).

As described above, the distal end frame 2 includes the plate-like member. In the distal end portion of the first example, a plate having a thickness of $T_S$ is used as the plate-like member. The distal end frame 2 has a bottom surface 2'. The illumination unit 4 has an exit surface 4'. In the distal end portion of the first example, the distal end frame 2 and the illumination unit 4 closely contact with each other. For this reason, no gap is generated between the bottom surface 2' and the exit surface 4'.

The illumination lens 5 is a plano-convex lens having a diameter $\phi$. A material having a refractive index $n_L$ is used for the illumination lens 5. The convex surface of the illumination lens 5 is a spherical surface having a curvature radius R. A curvature center C of the convex surface is positioned inside the illumination unit 4. It is possible to use an aspherical surface as the convex surface of the illumination lens 5. When the convex surface is an aspherical surface, R indicates a paraxial curvature radius.

The convex surface of the illumination lens 5 contacts a space filled with medium having a refractive index $n_W$. When the medium is the air, the value of the refractive index $n_W$ is 1. When the medium is water, the value of the refractive index $n_W$ is 1.33.

In the distal end portion of the first example, the exit surface 4' protrudes from the illumination lens 5 by a distance $L_{LL}$. The distance $L_{LL}$ is a distance between an edge P1 of the exit surface 4' and an edge PL of the illumination lens 5, and is a distance in a direction orthogonal to the optical axis of the illumination lens 5.

Illumination light emerges from the exit surface 4' in various directions. In the illumination light which emerged in various directions (hereinafter referred to as "illumination light group"), part of illumination light reaches the edge of the illumination lens 5.

In FIG. 2B, illumination light LB1 and illumination light LB1' are illustrated. The illumination light LB1 is illumination light which emerged from the edge P1 of the exit surface 4' and reached an edge P2 of the illumination lens 5. The illumination light LB1' is illumination light which emerged from the edge P2 of the illumination lens 5.

A straight line connecting the curvature center C of the convex surface and the edge P2 of the illumination lens 5 indicates a normal line of a plane at the edge P2 of the illumination lens 5. The normal line crosses the exit surface 4' at an angle $\theta_C$. The illumination light LB1 is incident on the convex surface of the illumination lens 5 at an incident angle $\theta_L$. The illumination light LB1' emerges from the convex surface of the illumination lens 5 at an angle of emergence $\theta'_L$.

Illumination light which emerged from the convex surface of the illumination lens 5 must be prevented from being directly incident on the image pickup unit. For this reason, the endoscope according to the present embodiment satisfies the following Conditional Expression (1).

$$\arcsin(n_L \times \sin\theta_L/n_W) \leq \arccos((\phi/2)/R) \quad (1)$$

The incident angle $\theta_L$ is used in the Conditional Expression (1). $\theta_L$ is expressed with the following expression.

$$\theta_L = \arccos((\phi/2)/R) - \arctan(T_S/L_I)$$

The distance $L_I$ is a distance between a predetermined intersection point and the edge P2 of the illumination lens 5, and is a distance in a direction orthogonal to the optical axis of the illumination lens 5. The predetermined intersection point is a point at which the light which emerged from the exit surface 4' crosses the bottom surface 2'.

In the distal end portion of the first example, the distal end frame 2 and the illumination unit 4 closely contact with each other. For this reason, the predetermined intersection point coincides with the edge P2 of the illumination lens 5. The distance $L_I$ is a distance between the edge P1 of the exit surface 4' and the edge P2 of the illumination lens 5. The distance between the edge P1 of the exit surface 4' and the edge P2 of the illumination lens 5 is "$\phi + L_{LL}$". Accordingly, "$L_I = \phi + L_{LL}$" is satisfied.

The illumination light LB1 is illumination light having the largest incident angle of rays of the illumination light which emerged from the edge P1 of the exit surface 4'. Accordingly, when the illumination light LB1' is not directly incident on the image pickup unit 3, rays of illumination light other than the illumination light LB1' are not directly incident on the image pickup unit 3, either. To achieve this, the Conditional Expression (1) may be satisfied when "$L_I = \phi + L_{LL}$" is satisfied. When the Conditional Expression (1) is satisfied, all the rays of illumination light which emerged from the edge P1 of the exit surface 4' are not directly incident on the image pickup unit 3.

Figure 3:
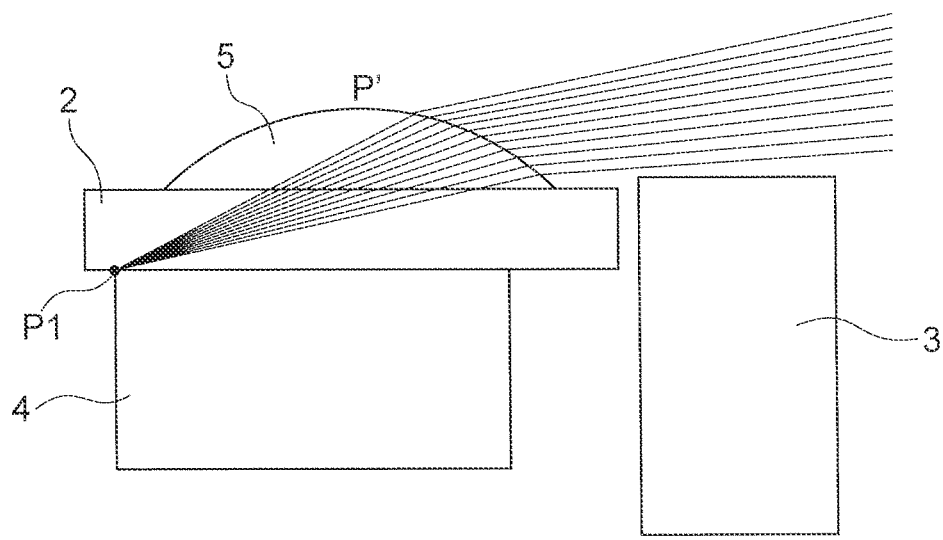
FIG. 3 is a diagram illustrating illumination light which emerged from an edge of an exit surface.

FIG. 3 is a diagram illustrating rays of illumination light which emerged from the edge of the exit surface. Rays of illumination light emerges from the edge P1 of the exit surface in addition to the illumination light LB1. The illumination light LB1 is illumination light having the largest incident angle in the rays of illumination light which emerged from the edge P1 of the exit surface. The incident angles of the rays of illumination light other than the illumination light LB1 are smaller than the incident angle $\theta_L$.

In this case, the rays of illumination light other than the illumination light LB1 emerge from the convex surface of the illumination lens 5 at angles smaller than the angle of emergence $\theta'L$. When the illumination light LB1' satisfies the Conditional Expression (1), the rays of illumination light other than the illumination light LB1' are not directly incident on the image pickup unit 3, as illustrated in FIG. 3.

However, in the exit surface 4', illumination light emerges from parts other than the edge P1 of the exit surface. For this reason, the illumination light LB1 is not always illumination light having the largest incident angle in the illumination light group. To prevent all the rays of illumination light from being directly incident on the image pickup unit 3, the illumination light having the largest incident angle in the illumination light group may satisfy the Conditional Expression (1).

At the illumination light having the largest incident angle in the illumination light group, a value of the distance $L_{LL}$ is maximum. For this reason, the distance in the illumination light having the largest incident angle is referred to as "distance $L_{LLmax}$". In this case, in the distal end portion of the first example, "$L_I = \phi + L_{LLmax}$" is satisfied. Accordingly, the Conditional Expression (1) may be satisfied when "$L_I = \phi + L_{LLmax}$" is satisfied.

Figure 4:
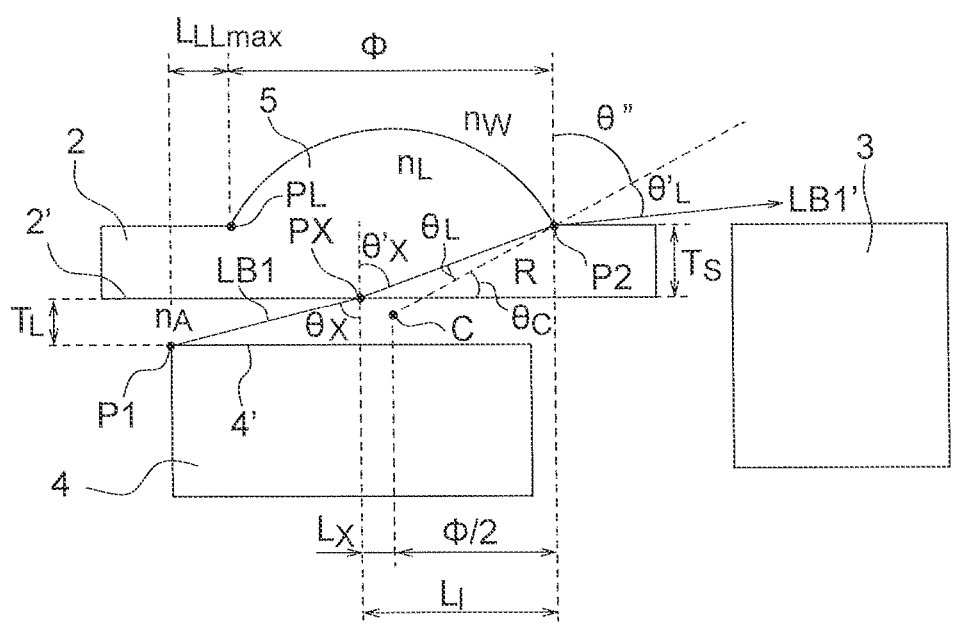
FIG. 4 is a sectional view of the distal end portion of the endoscope according to the present embodiment.

FIG. 4 is a diagram illustrating the distal end portion of the endoscope according to the present embodiment. FIG. 4 illustrates a section of the distal end portion of a second example. The same reference numerals are assigned to the same constituent elements as those of the distal end portion of the first example, and an explanation thereof will be omitted.

In the distal end portion of the second example, the distal end frame 2 and the illumination unit 4 are not in close contact with each other. For this reason, a gap is generated between the bottom surface 2' and the exit surface 4'. In the distal end portion of the second example, the distal end frame 2 and the illumination unit 4 are separated by a distance $T_L$. The distance $T_L$ is a distance between the exit surface 4' and the distal end frame 2, more specifically, a distance between the exit surface 4' and the bottom surface 2'.

When the distal end frame 2 and the illumination unit 4 are separated from each other, a space between the exit surface 4' and the bottom surface 2' is filled with a medium having a refractive index $n_A$. When the medium is the air, the value of the refractive index $n_A$ is 1.

In FIG. 4, illumination light LB1 and illumination light LB1' are illustrated. The illumination light LB1 is illumination light which emerged from the edge P1 of the exit surface 4' and reached a predetermined intersection point PX. The predetermined intersection point PX is a point at which the light which emerged from the exit surface 4' crosses the bottom surface 2'. The illumination light LB1 is incident on the bottom surface 2' at an incident angle $\theta_X$.

The illumination light LB1 incident at the incident angle $\theta_X$ emerges from the bottom surface 2' at an angle of emergence $\theta_X'$, and reaches the edge P2 of the illumination lens 5. The illumination light LB1' is illumination light which emerged from the edge P2 of the illumination lens 5.

In the distal end portion of the second example, the illumination light LB1 is illumination light having the largest incident angle in the illumination light group. For this reason, in FIG. 4, the distance $L_{LLmax}$ is used instead of the distance $L_{LL}$ in FIG. 2B.

As described above, the incident angle $\theta_L$ is used in the Conditional Expression (1). $\theta_L$ is expressed with the following expression.

$$\theta L = \arccos((\phi/2)/R) - \arctan(T_S/L_I)$$

The distance $L_I$ is a distance between the predetermined intersection point PX and the edge P2 of the illumination lens 5, and a distance in a direction orthogonal to the optical axis of the illumination lens 5.

In the distal end portion of the second example, the distal end frame 2 and the illumination unit 4 are not in close contact with each other. For this reason, the predetermined intersection point PX does not coincide with the edge P2 of the illumination lens 5. The distance $L_I$ is a distance between the predetermined intersection point PX and the edge P2 of the illumination lens 5. The distance between the predetermined intersection point PX and the edge P2 of the illumination lens 5 is "$\phi/2 + L_X$". Accordingly, "$L_I = \phi/2 + L_X$" is satisfied.

$L_X$ is calculated from the following expressions (A), (B), and (C), $$\sin \theta_X'/\sin \theta_X = n_L/n_A \quad (A)$$

$$\tan(90° - \theta_X) = T_L/((\phi/2) - L_X + L_{LLmax}) \quad (B)$$

$$\tan(90° - \theta_X') = T_S/((\phi/2) + L_X) \quad (C)$$

where, $n_A$ is a refractive index of a medium between the exit surface and the distal end frame, $\theta_X$ is an incident angle of a light beam incident on the distal end frame, and $\theta_X'$ is an angle of emergence of a light beam which emerges from the distal end frame.

The illumination light LB1 is illumination light having the largest incident angle of the rays of illumination light which emerged from the edge of the exit surface 4'. Accordingly, when the illumination light LB1' is not directly incident on the image pickup unit 3, the rays of illumination light other than the illumination light LB1' are not directly incident on the image pickup unit 3, either. To achieve this, the Conditional Expression (1) may be satisfied when "$L_I = \phi/2 + L_X$" is satisfied. When the Conditional Expression (1) is satisfied, all the rays of illumination light which emerged from the edge of the exit surface 4' are not directly incident on the image pickup unit 3.

Both in the distal end portion of the first example and the distal end portion of the second example, when the Conditional Expression (1) is satisfied, the illumination light which emerged from the illumination lens is not directly incident on the image pickup unit. Therefore, it is possible to prevent generation of a ghost or a flare and achieve illumination with high illumination efficiency and high light distribution property.

In the endoscope according to the present embodiment, it is preferable that the following Conditional Expression (2) be satisfied:

$$\arcsin(n_L \times \sin \theta_M/n_W) \leq \arccos((\phi/2)/R) \quad (2)$$

where, $n_L$ is the refractive index of the illumination lens, $n_W$ is the refractive index of a medium in a space contacting the illumination lens, R is the curvature radius of a convex surface of the illumination lens, $T_S$ is the thickness of the distal end frame, $\phi$ is the diameter of the illumination lens, $\theta_M$ is calculated by $\arccos((\phi/2)/R) - \arctan(T_S/(L_Y + \phi/2))$, $L_Y$ is a distance between the curvature center of the illumination lens and the predetermined exit point, and a distance in a direction orthogonal to the optical axis of the illumination lens, and the predetermined exit point is a point from which illumination light traveling toward the image pickup unit and having the largest incident angle emerges.

Figure 5A:
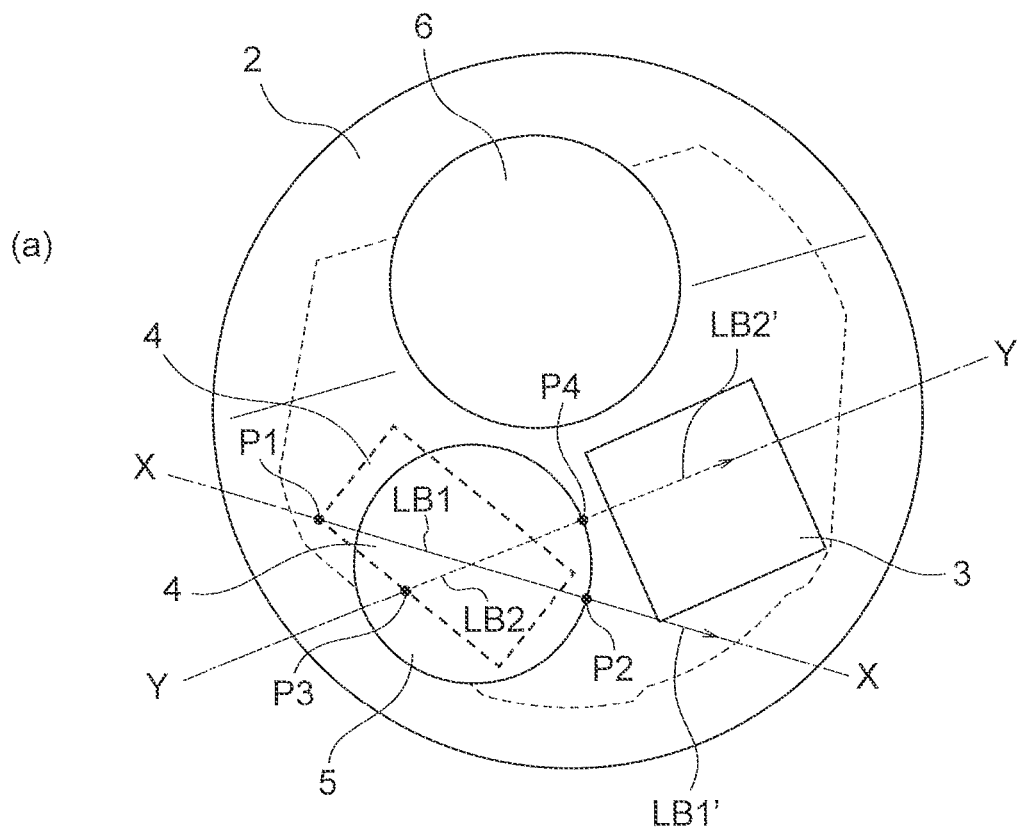
FIG. 5A and FIG. 5B are diagrams illustrating the distal end portion of the endoscope according to the present embodiment.
Figure 5B:
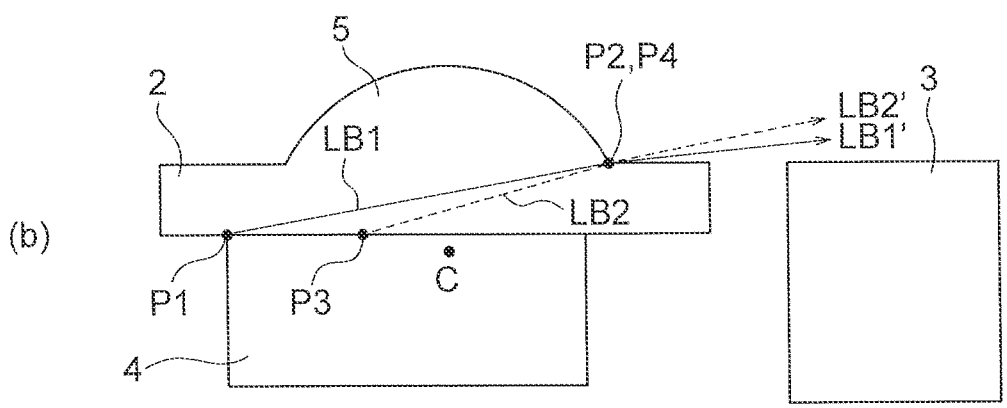
Figure 6:
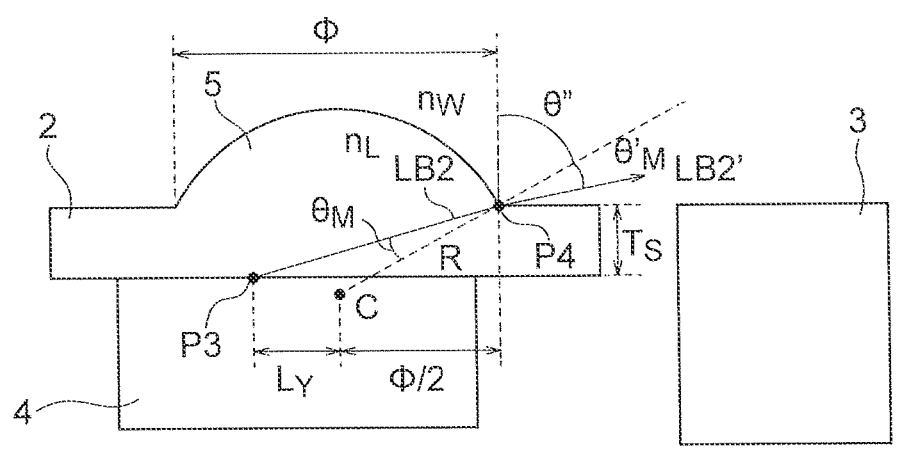
FIG. 6 is a sectional view of the distal end portion of the endoscope according to the present embodiment.

FIG. 5A and FIG. 5B are diagrams illustrating a distal end portion of the endoscope according to the present embodiment. FIG. 5A is a front view of the distal end portion, and FIG. 5B is a sectional view of the distal end portion. The same reference numerals are assigned to the same constituent elements as those in FIG. 2, and an explanation thereof will be omitted. FIG. 6 is a sectional view of the distal end portion of the endoscope according to the present embodiment. FIG. 6 illustrates parameters used in the Conditional Expression (2).

As illustrated in FIG. 5A, illumination light LB1' passes through the corner of the image pickup unit 3. In this case, the possibility that the illumination light LB1' is directly incident on the image pickup unit 3 is very low. Accordingly, even the illumination light having the largest incident angle in the illumination light group is not required to satisfy the Conditional Expression (1), when the illumination light is not illumination light traveling toward the image pickup unit 3.

In other words, illumination light traveling toward the image pickup unit 3 and having the largest incident angle in the illumination light group may satisfy the Conditional Expression (1). By making such arrangement, the illumination light which emerges from the illumination lens is not directly incident on the image pickup unit.

The sectional view illustrated in FIG. 5B is a diagram obtained by superimposing a sectional view taken along a straight line X-X on a sectional view taken along a straight line Y-Y illustrated in FIG. 5A. In FIG. 5A and FIG. 5B, the illumination light LB1 and the illumination light LB1' are illustrated with solid lines, and illumination light LB2 and illumination light LB2' are illustrated with broken lines. An explanation of the illumination light LB1 and the illumination light LB1' will be omitted.

The illumination light LB2 is illumination light which emerged from an edge P3 of the exit surface and reached an edge P4 of the illumination lens 5. The illumination light LB2' is illumination light which emerged from the edge P4 of the illumination lens.

As illustrated in FIG. 5A, the illumination light LB2 is illumination light traveling toward the image pickup unit 3 of the illumination light group. In addition, the illumination light LB2 is illumination light having the largest incident angle of the rays of illumination light which emerged from the edge P3 of the exit surface. Accordingly, the illumination light LB2' may not be directly incident on the image pickup unit 3.

The illumination light traveling toward the image pickup unit 3 emerges from parts other than the edge P3 of the exit surface. For this reason, the illumination light LB2 does not always correspond to the illumination light traveling toward the image pickup unit 3 and having the smallest incident angle of the illumination light group. Accordingly, the illumination light traveling toward the image pickup unit 3 and having the largest incident angle of the illumination light group may satisfy the Conditional Expression (2) instead of the Conditional Expression (1).

When the Conditional Expression (2) is satisfied, the illumination light which emerges from the illumination lens is not directly incident on the image pickup unit. Therefore, it is possible to prevent generation of a ghost or a flare and to achieve illumination with high illumination efficiency and high light distribution property.

In the endoscope according to the present embodiment, it is preferable that the following Conditional Expression (3) be satisfied:

$$\theta'_{max} + \theta'' \leq 90° \quad (3)$$

where, $\theta'_{max}$ is an angle of emergence of predetermined illumination light, $\theta''$ is an angle between a first straight line and a second straight line, the predetermined illumination light is illumination light having the largest incident angle at an edge of the illumination lens of rays of illumination light which emerged from the exit surface, the first straight line is a straight line through the curvature center of the illumination lens and the edge of the illumination lens, and the second straight line is a straight line through the edge of the illumination lens and parallel to the optical axis of the illumination lens.

The angle of emergence of the predetermined illumination light is an angle of emergence at which the predetermined illumination light emerges from the edge of the illumination lens. When the Conditional Expression (3) is satisfied, the illumination light which emerges from the illumination lens is not directly incident on the image pickup unit. Therefore, it is possible to prevent generation of a ghost or a flare and to achieve illumination with high illumination efficiency and high light distribution property.

In the endoscope according to the present embodiment, it is preferable that the distal end frame and the illumination lens be integrated.

As illustrated in FIG. 2B, it is possible that the distal end frame 2 and the illumination lens 5 are integrated. In this case, because no boundary exists between the distal end frame 2 and the illumination lens 5, it is possible to enhance the strength of the distal end frame. In addition, the distal end portion is easily assembled.

In the endoscope according to the present embodiment, it is preferable that the distal end frame and the illumination lens be separated.

Figure 7:
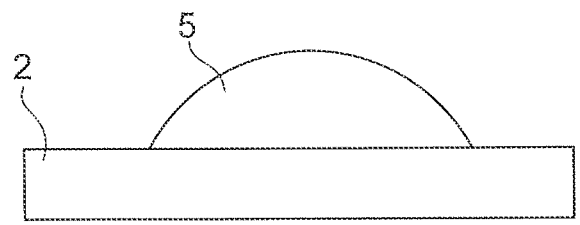
FIG. 7 is a sectional view of the distal end portion of the endoscope according to the present embodiment.

FIG. 7 is a diagram illustrating the distal end portion of the endoscope according to the present embodiment. As illustrated in FIG. 7, it is possible that the distal end frame 2 and the illumination lens 5 are separated. In this case, the number of types of material that can be used for the illumination lens 5 increases. Therefore, it is possible to enhance the light distribution property of the illumination light.

In the endoscope according to the embodiment, it is preferable that the illumination unit have a rectangular exit surface, the exit surface include a first region and a second region, only the first region be covered with the illumination lens, and the first region include an exit region of illumination light having the maximum light intensity.

By using an LED in the illumination unit, it is possible to achieve reduction in size of the endoscope, reduction in power consumption, and reduction in cost. The LED has a circular light exit surface or a rectangular light exit surface. By using an LED having a rectangular light exit surface, it is possible to efficiently use a space at the distal end of the insertion part. As a result, it is possible to reduce the diameter of the distal end of the insertion part.

When the whole light exit surface is covered with the illumination lens, it is possible to improve efficiency of illumination light and/or light distribution. However, when the shape of the light exit surface is a rectangular shape, the diameter of the illumination lens increases. For this reason, the distal end of the insertion part becomes large. Moreover, when the illumination lens is not used, it is not possible to distribute the illumination light as desired. In this case, because the radiation efficiency deteriorates, the light quantity of the illumination light becomes insufficient.

Figure 8:
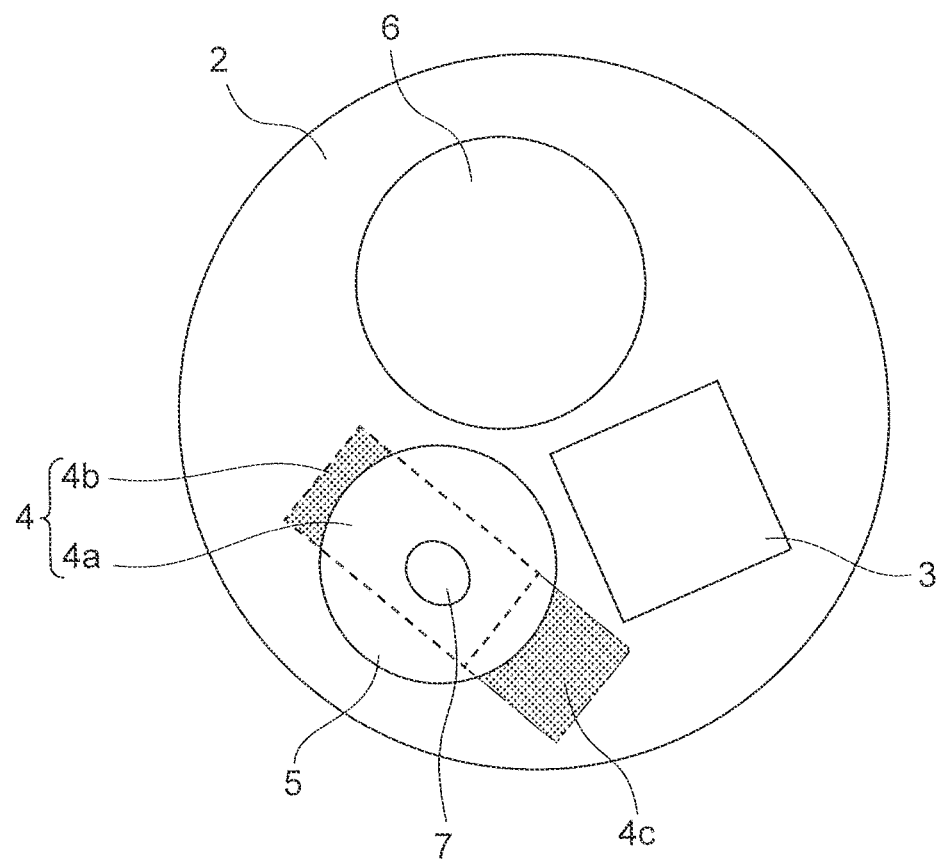
FIG. 8 is a diagram illustrating the distal end portion of the endoscope according to the present embodiment.

FIG. 8 is a diagram illustrating the distal end portion of the endoscope according to the present embodiment. FIG. 8 illustrates an exit region of illumination light having the maximum light intensity.

As illustrated in FIG. 8, in the endoscope according to the present embodiment, the illumination unit 4 has a rectangular exit surface. The exit surface includes a first region 4a and a second region 4b. Only the first region 4a is covered with the illumination lens 5. The exit region 7 is included in the first region 4a.

The exit region 7 is an exit region of illumination light having the maximum light intensity. Therefore, it is possible to distribute the illumination light as desired and sufficiently secure the light quantity of the illumination light, while the diameter of the illumination lens 5 is reduced. As a result, it is possible to achieve high radiation efficiency and high light distribution property, while the diameter of the distal end of the insertion part is reduced.

In the exit region 7, it is preferable that the light intensity be maximum throughout the whole area. However, there are cases where it is difficult to achieve the maximum light intensity throughout the whole area. For this reason, a slight difference in light intensity may exist. It is preferable that the difference in light intensity be small as much as possible.

When the size of the illumination unit 4 is increased, the exit surface protrudes to the image pickup unit 3 side in some cases. Specifically, a third region 4c is generated. In FIG. 8, the third region 4c protrudes more than the first region 4a.

Part of illumination light which emerged from the third region 4c is incident on the illumination lens 5, and thereafter emerges from the illumination lens 5. However, the third region 4c is positioned closer to the image pickup unit 3 than the illumination lens 5. In this case, the illumination light which emerges from the illumination lens 5 is not incident on the image pickup unit 3. For this reason, it is unnecessary to consider generation of a flare or a ghost with respect to the third region 4c. By contrast, it is necessary to consider generation of a flare or a ghost with respect to the first region 4a.

The Conditional Expression (1) is a conditional expression relating to generation of a flare or generation of a ghost. In the Conditional Expression (1), the maximum distance $L_{LLmax}$ is used. The maximum distance $L_{LLmax}$ is a distance relating to the edge of the exit surface and the edge of the illumination lens.

As described above, it is necessary to consider generation of a flare or generation of a ghost with respect to the first region 4a. For this reason, the maximum distance $L_{LLmax}$ may be determined on the basis of the first region 4a. The first region 4a is positioned on a side opposite to the image pickup unit 3, with the illumination lens 5 interposed therebetween. Accordingly, the maximum distance $L_{LLmax}$ is determined on the basis of the edge of the exit surface positioned in a direction opposite to the image pickup unit.

In FIG. 8, the first region 4a is a region protruding from the illumination lens 5. However, the first region 4a may be covered with the illumination lens 5. Also in this case, the first region 4a is positioned on a side opposite to the image pickup unit 3, with the illumination lens 5 interposed therebetween. Accordingly, it is possible to determine the maximum distance $L_{LLmax}$ on the basis of the first region 4a.

It is preferable that the endoscope according to the present embodiment include a forceps channel, the illumination unit have a rectangular exit surface, a crescent-shaped region be defined by the outer diameter at the distal end of the insertion part and a circular shape of the forceps channel, and the long-side direction of the exit surface substantially coincide with the circumferential direction of the crescent-shaped region.

By making such arrangement, it is possible to efficiently use the space at the distal end of the insertion part. Consequently, it is possible to reduce the diameter of the distal end of the insertion part.

Figure 9:
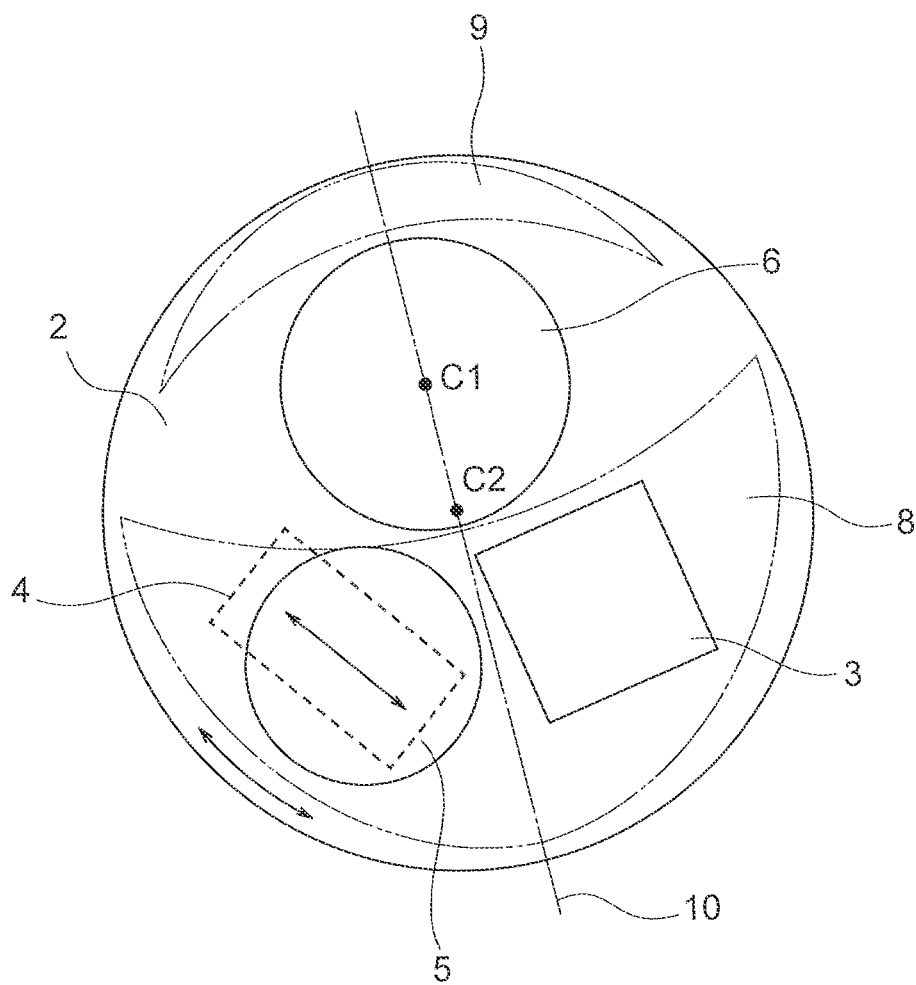
FIG. 9 is a diagram illustrating the distal end portion of the endoscope according to the present embodiment.

FIG. 9 is a diagram illustrating the distal end portion of the endoscope according to the present embodiment. FIG. 9 illustrates the crescent-shaped region.

It is possible to provide a forceps channel 6 in the endoscope according to the present embodiment. The illumination lens 5 is disposed in the distal end frame 2. In addition, the distal end frame 2 includes a transmission region to cause the light from the object to reach the image pickup unit 3. The forceps channel 6 is provided in a position in which the forceps channel 6 overlaps neither the illumination lens 5 nor the transmission region. For this reason, in many cases, the forceps channel 6 is provided in a position eccentric with respect to the center of the distal end frame 2.

The endoscope according to the present embodiment includes the forceps channel 6. In this case, a region held between the outer circumference of the forceps channel 6 and the outer circumference of the distal end frame 2 is formed in the distal end frame 2. In this example, both the outer circumference of the forceps channel 6 and the outer circumference of the distal end frame 2 have a circular shape. In this case, a region 8 and a region 9 are positioned on a straight line 10 through the center C1 of the forceps channel 6 and the center C2 of the distal end frame 2. Each of the region 8 and the region 9 is a region held between the outer circumference of the forceps channel 6 and the outer circumference of the distal end frame 2.

On the straight line 10, the width of the region 8 is larger than the width of the region 9. Specifically, the region 8 is wider than the region 9. Accordingly, the illumination lens 5, the transmission region (image pickup unit 3), and the illumination unit 4 are positioned in the region 8.

The region 8 is a crescent-shaped region. As illustrated in FIG. 9, the long-side direction of the exit surface substantially coincides with the circumferential direction of the region 8. Therefore, it is possible to efficiently use the space at the distal end of the insertion part.

Example of Values of parameters are given below. Unit of length is mm and unit of angle is degree.

| | |
|---|---|
| $n_L$ | 1.585 |
| $n_w$ | 1.33 |
| R | 0.7 |
| $T_S$ | 0.2 |
| φ | 1 |
| $L_{LLmax}$ | 0.12 |
| $L_I$ | 1.12 |
| $θ_L$ | 34.29 |
| $θ'_L$ | 42.18 |
| $θ''$ | 45.58 |
| $θ'' + θ'_L$ | 87.76 |

Moreover, in the present disclosure, following disclosures are included.

APPENDIX MODE 1

An endoscope comprising:
a distal end frame disposed at a distal end of an insertion part;
an image pickup unit disposed inside the insertion part;
an illumination unit disposed inside the insertion part; and
an illumination lens disposed on a side opposite to the illumination unit with the distal end frame interposed therebetween, wherein
the illumination lens is a plano-convex lens and disposed with a flat surface thereof facing the illumination unit,
the illumination unit includes an exit surface in which illumination light emerges, and
the following Conditional Expression (1) is satisfied:

$$\arc\sin(n_L \times \sin\theta_L/n_W) \leq \arc\cos((\phi/2)/R) \quad (1)$$

where,
$n_L$ is a refractive index of the illumination lens,
$n_W$ is a refractive index of a medium in a space contacting the illumination lens,
R is a curvature radius of a convex surface of the illumination lens,
$T_S$ is a thickness of the distal end frame,
$\phi$ is a diameter of the illumination lens,
$\theta_L = \arccos((\phi/2)/R) - \arctan(T_S/L_I)$,
$L_I = \phi/2 + L_X$ when $T_L > 0$ is satisfied, $L_I = +L_{LLmax}$ when $T_L = 0$ is satisfied,
$T_L$ is a distance between the exit surface and the distal end frame,
$L_{LLmax}$ is a maximum distance between an edge of the exit surface positioned in a direction opposite to the image pickup unit and an edge of the illumination lens,
sign of the maximum distance is positive when the exit surface protrudes from the illumination lens, and negative when the exit surface is completely covered with the illumination lens,
$L_X$ is calculated from the following expressions (A), (B), and (C), $$\sin\theta_X'/\sin\theta_X = n_L/n_A \quad (A)$$

$$\tan(90° - \theta_X) = T_L/((\phi/2) - L_X + L_{LLmax}) \quad (B)$$

$$\tan(90° - \theta_X') = T_S/((\phi/2) + L_X) \quad (C)$$

where,
$n_A$ is a refractive index of a medium between the exit surface and the distal end frame,
$\theta_X$ is an incident angle of a light beam incident on the distal end frame, and
$\theta_X'$ is an angle of emergence of a light beam which emerges from the distal end frame.

APPENDIX MODE 2

The endoscope according to Appendix mode 1, wherein the following Conditional Expression (2) is satisfied:

$$\arc\sin(n_L \times \sin\theta_M/n_W) \leq \arc\cos((\phi/2)/R) \quad (2)$$

where,
$\theta_M$ is calculated by $\arc\cos((\phi/2)/R) - \arc\tan(T_S/(L_\gamma + \phi/2))$
$L_\gamma$ is a distance between a curvature center of the illumination lens and a predetermined exit point, and a distance in a direction orthogonal to an optical axis of the illumination lens, and the predetermined exit point is a point from which illumination light traveling toward the image pickup unit and having a largest incident angle emerges.

APPENDIX MODE 3

The endoscope according to Appendix mode 1, wherein the following Conditional Expression (3) is satisfied:

$$\theta'_{max} + \theta'' \leq 90° \quad (3)$$

where,
$\theta'_{max}$ is an angle of emergence of the predetermined illumination light,
$\theta''$ is an angle between a first straight line and a second straight line,
the predetermined illumination light is illumination light having the largest incident angle at an edge of the illumination lens of rays of illumination light which emerged from the exit surface,
the first straight line is a straight line through a curvature center of the illumination lens and the edge of the illumination lens, and
the second straight line is a straight line through the edge of the illumination lens and parallel to an optical axis of the illumination lens.

APPENDIX MODE 4

The endoscope according to Appendix mode 1, wherein the distal end frame and the illumination lens are integrated.

APPENDIX MODE 5

The endoscope according to Appendix mode 1, wherein the distal end frame and the illumination lens are separated.

APPENDIX MODE 6

The endoscope according to Appendix mode 1, wherein the illumination unit has a rectangular exit surface, the exit surface includes a first region and a second region,
only the first region is covered with the illumination lens, and
the first region includes an exit region of illumination light having a maximum light intensity.

APPENDIX MODE 7

The endoscope according to Appendix mode 1, further comprising:
a forceps channel, wherein
the illumination unit has a rectangular exit surface,
a crescent-shaped region is defined by an outer diameter at the distal end of the insertion part and a circular shape of the forceps channel, and
a long-side direction of the exit surface substantially coincides with a circumferential direction of the crescent-shaped region.

According to the present disclosure, it is possible to provide an endoscope suppressing generation of a flare or generation of a ghost.

As described above, the present disclosure is suitable for an endoscope suppressing generation of a flare or generation of a ghost.

What is claimed is:

1. An endoscope comprising:
   a distal end frame disposed at a distal end of an insertion part;
   an image pickup unit disposed inside the insertion part;
   an illumination unit disposed inside the insertion part; and
   an illumination lens disposed on a side of the distal end frame opposite to the illumination unit,
   wherein:
   the illumination lens is a plano-convex lens and disposed with a flat surface thereof towards the illumination unit,
   the illumination unit includes an exit surface at which illumination light emerges,
   the flat surface of the illumination lens and the illumination unit are (i) arranged with only a space between the flat surface and the illumination unit and no lens element between the flat surface and the illumination unit, or (ii) arranged in contact with each other without any lens element between the flat surface and the illumination unit,
   a convex surface of the plano-convex lens protrudes with respect to the distal end frame, and
   the following Conditional Expression (1) is satisfied:

$$\arcsin(n_L \times \sin \theta_L / n_W) \leq \arccos((\phi/2)/R) \qquad (1)$$

where,
   $n_L$ is a refractive index of the illumination lens,
   $n_W$ is a refractive index of a medium in a space contacting the illumination lens,
   R is a curvature radius of the convex surface of the illumination lens,
   $T_S$ is a thickness of the distal end frame,
   $\phi$ is a diameter of the illumination lens,
   $\theta_L = \arccos((\phi/2)/R) - \arctan(T_S/L_I)$,
   $L_I = \phi/2 + L_X$ when $T_L > 0$ is satisfied, $L_I = \phi + L_{LLmax}$ when $T_L = 0$ is satisfied,
   $T_L$ is a distance between the exit surface and the distal end frame,
   $L_{LLmax}$ is a maximum distance between an edge of the exit surface positioned in a direction opposite to the image pickup unit and an edge of the illumination lens,
   a sign of the maximum distance is positive when the exit surface protrudes from the illumination lens, and negative when the exit surface is completely covered with the illumination lens,
   $L_X$ is calculated from the following expressions (A), (B), and (C), $$\sin \theta_X' / \sin \theta_X = n_L / n_A \qquad (A)$$

$$\tan(90° - \theta_X) = T_L / ((\phi/2) - L_X + L_{LLmax}) \qquad (B)$$

$$\tan(90° - \theta_X') = T_S / ((\phi/2) + L_X) \qquad (C)$$

where,
   $n_A$ is a refractive index of a medium between the exit surface and the distal end frame,
   $\theta_X$ is an incident angle of a light beam incident on the distal end frame, and
   $\theta_X'$ is an angle of emergence of a light beam which emerges from the distal end frame.

2. The endoscope according to claim 1, wherein the following Conditional Expression (2) is satisfied:

$$\arcsin(n_L \times \sin \theta_M / n_W) \leq \arccos((\phi/2)/R) \qquad (2)$$

where,
   $\theta_M$ is calculated by $\arccos((\phi/2)/R) - \arctan(T_S/(L_\gamma + \phi/2))$,
   $L_\gamma$ is a distance between a curvature center of the illumination lens and a predetermined exit point, in a direction intersecting an optical axis of the illumination lens, and
   the predetermined exit point is a point from which illumination light traveling toward the image pickup unit and having a largest incident angle emerges.

3. The endoscope according to claim 1, wherein the following Conditional Expression (3) is satisfied:

$$\theta'_{max} + \theta'' \leq 90° \qquad (3)$$

where,
   $\theta'_{max}$ is an angle of emergence of the predetermined illumination light,
   $\theta''$ is an angle between a first straight line and a second straight line,
   the predetermined illumination light is illumination light having a largest incident angle at the edge of the illumination lens from among rays of illumination light which emerged from the exit surface,
   the first straight line is a straight line through a curvature center of the illumination lens and the edge of the illumination lens, and
   the second straight line is a straight line through the edge of the illumination lens and parallel to an optical axis of the illumination lens.

4. The endoscope according to claim 1, wherein the distal end frame and the illumination lens are integrated.

5. The endoscope according to claim 1, wherein the distal end frame and the illumination lens are separated.

6. The endoscope according to claim 1, wherein:
   the exit surface of the illumination unit is rectangular,
   the exit surface includes a first region and a second region,
   only the first region is covered with the illumination lens, and
   the first region includes an exit region of illumination light having a maximum light intensity.

7. The endoscope according to claim 1, further comprising:
   a forceps channel,
   wherein:
   the exit surface of the illumination unit is rectangular,
   a crescent-shaped region is defined between (i) an outer circumference of the distal end frame and (ii) an outer circumference of the forceps channel, and
   a long-side direction of the exit surface substantially coincides with a circumferential direction of the crescent-shaped region.

* * * * *